(12) United States Patent
Li

(10) Patent No.: US 7,553,506 B2
(45) Date of Patent: Jun. 30, 2009

(54) HERBAL COMPOSITIONS FOR PREVENTION AND TREATMENT OF RHEUMATIC AND INFLAMMATORY DISEASES AND METHOD OF PREPARING THE SAME

(75) Inventor: YanXue Li, Guangdong (CN)

(73) Assignee: Shenzhen Qianrenren Sci. & Tech. Development Co., Shenzhen, Guangdon (CN)

( * ) Notice: Subject to any disclaimer, the term of this patent is extended or adjusted under 35 U.S.C. 154(b) by 452 days.

(21) Appl. No.: 11/148,407

(22) Filed: Jun. 9, 2005

(65) Prior Publication Data

US 2005/0276873 A1 Dec. 15, 2005

Related U.S. Application Data

(60) Provisional application No. 60/578,127, filed on Jun. 9, 2004.

(51) Int. Cl.
*A61K 36/00* (2006.01)
(52) U.S. Cl. .......................... 424/773; 424/725
(58) Field of Classification Search .................. None
See application file for complete search history.

(56) References Cited

U.S. PATENT DOCUMENTS

| 6,939,571 B2 * | 9/2005 | Zuo | 424/748 |
| 2003/0143290 A1 * | 7/2003 | Cho et al. | 424/728 |

FOREIGN PATENT DOCUMENTS

| CN | 1117391 | * | 2/1996 |
| CN | 1122242 | * | 5/1996 |
| CN | 1129571 | * | 8/1996 |
| CN | 1140086 | * | 1/1997 |
| CN | 1142968 | * | 2/1997 |
| CN | 1154863 | * | 7/1997 |
| CN | 1175441 | * | 3/1998 |
| CN | 1279079 | * | 1/2001 |
| CN | 1325691 | * | 12/2001 |
| CN | 1333028 | * | 1/2002 |
| CN | 1350852 | * | 5/2002 |
| CN | 1356133 | * | 7/2002 |
| CN | 1365827 | * | 8/2002 |
| CN | 1383853 | * | 12/2002 |

* cited by examiner

*Primary Examiner*—Christopher R. Tate
(74) *Attorney, Agent, or Firm*—Bei & Ocean; George G. Wang

(57) ABSTRACT

This invention provides two novel herbal compositions. The first herbal composition contains Radix Clematidis, Radix Angelicae Pubescentis, Rhizoma et Radix Notopterygii, Radix Saposhnikoviae, Radix Gentianae Macrophyllae. The second herbal composition contains Radix Angelicae Sinensis, Rhizoma Chuanxiong, Cortex Eucommiae, and Radix Achyranthis Bidentataeas. It is preferred to mix the two herbal compositions together to achieve preventive and therapeutic effects on inflammatory and rheumatic arthritic diseases in human and livestock. The herbal compositions of the present invention can be used as a pharmaceutical composition, a dietary supplement or a feed. This invention also provides processes for making the herbal compositions.

26 Claims, 4 Drawing Sheets

HERBAL COMPOSITIONS FOR PREVENTION AND TREATMENT OF RHEUMATIC AND INFLAMMATORY DISEASES AND METHOD OF PREPARING THE SAME

RELATED INVENTION

The present invention claims the priority of U.S. Provisional Application Ser. No. 60/578,127, filed on Jun. 9, 2004, which is herein incorporated by reference.

FIELD OF THE INVENTION

The present invention relates to two novel herbal compositions. The first herbal composition comprises Radix Clematidis, Radix Angelicae Pubescentis, Rhizoma et Radix Notopterygii, Radix Saposhnikoviae, and Radix Gentianae Macrophyllae. The second herbal composition comprises Rhizoma Chuanxiong, Radix Angelicae Sinensis, Cortex Eucommiae, and Radix Achyranthis Bidentataeas. It is preferred to combine the first and the second herbal compositions together to achieve maximal preventive and therapeutic effects on alleviating symptoms associated with inflammatory and rheumatic diseases. The present invention also relates to methods for preparing and using the herbal compositions.

BACKGROUND OF THE INVENTION

Rheumatism refers to any of several pathological conditions of the muscles, tendons, joints, bones, or nerves, characterized by discomfort and disability. It is estimated that over 100 rheumatic diseases affect the joints and other connective tissues of animals.

Arthritis is an autoimmune disease characterized by their symptoms such as pain, swelling and stiffness in the joints. The two major forms of arthritis in mammals are inflammatory arthritis such as rheumatoid arthritis (RA), and osteoarthritis (OA), a progressive, degenerative loss of cartilage often secondary to mechanical stress, aging, dysplastic conditions and/or injury. The symptoms of arthritis generally relate to arthrosis of spine, e.g., hallux rigidus, arthrosis psoriaticum and rheumatic arthritis.

Rheumatoid arthritis (RA) is a common autoimmune disease characterized by joint swelling, deformation and ultimately, destruction, culminating in severe physical disability. Rheumatic diseases include diseases of the muscles, tendons, joints, bones or sinews, which are generally characterized by inflammation and/or degeneration. Approximately 1 to 2% of the population suffer from rheumatoid arthritis, which is characterized by an imbalance in the immune system that causes an overproduction of pro-inflammatory cytokines, e.g., TNF-.alpha., IL-1 and a lack of anti-inflammatory cytokines, e.g., IL-10, Il-1. RA is characterized by synovial inflammation, which progresses to cartilage destruction, bone erosion and subsequent joint deformity. During the inflammatory process, polymorphonuclear cells, macrophages and lymphocytes are released. Activated T-lymphocytes produce cytotoxins and pro-inflammatory cytokines, while macrophages stimulate the release of the prostaglandins and cytotoxins. Vasoactive substances (histamine, kinins and prostaglandins) are released at the site of inflammation and cause edema, warmth, erythema and pain associated with inflamed joints.

Most of the current treatments are directed to the correction of immune aberration that supposedly drives the synovial cell proliferation and cartilage erosion. Present treatment of arthritis includes first line drugs for controlling pain and inflammation classified as non-steroidal anti-inflammatory drugs (NSAIDs), e.g., aspirin, ibuprofen, naproxen, etc. Secondary treatment of arthritis includes corticosteroids, slow acting antirheumatic drugs (SAARDs) or disease-modifying anti-rheumatic drugs (DMARDs), e.g., methotrexate, penicillinamine, cyclophosphamide, gold salts, azothipoprine, levamisole, etc.

The use of glucocorticoides and non-steroidal anti-inflammatory drugs (NSAIDs) in treating RA has been known for quite some time and are considered conservative treatment for RA. Corticosteroids, the synthetic versions of the body's cortisone hormone, are used to inhibit RA progression. They effectively reduce inflammation and suppress auto-immunity. The most commonly prescribed corticosteroids are prednisone and dexamthasone. Long-term use of dexamthasone, however, can produce such side effects as weight gain, rounding of the face, thinning of the skin and bone, acne, easy bruising, high blood pressure, and an increased risk of diabetes, infection and stomach ulcers. As a result, they are generally used only for short periods of time during acute flare-ups.

Among the disease-modifying anti-rheumatic drugs (DMARDs), methotrexate (MTX) became a benchmark agent for its efficacy and tolerability in the early phase of RA and the recent FDA approved leflunomide, an inhibitor of dihydro-orotate dehydrogenase, is known for its efficacy in treating RA, even though the specific mechanism of action of leflunomide is not yet known. However, most of the DMARDs have potential long-term side effects and toxicity. For example, the use of leflunomide may affect the lymphocyte function in vivo and in vitro.

Recently, another group of drugs called biological-response modifiers (BRMs) has also been developed for treatment of RA. The first group of BRMs approved for treatment of RA includes the antagonists to TNF-α, which work through binding to its receptor or directly binding to the TNF-α protein. However, BRM therapy, despite substantial efficacy and clinical improvement, entails high cost and hypersensitivity to the medications and infections due to TNF-α blockage.

Action mechanism of all of these drugs is based on suppression of inflammatory reaction. To our knowledge, no drugs have been developed for cartilage protection. Also, most of these drugs have various toxic, particularly cytotoxic, side effects. Thus, these drugs have limited advantages and their effects are mainly of short-term duration. The side effects of these drugs, e.g., gastric erosion which has adverse effects on kidneys and liver, dictate against their use over extended periods of time. Further, the drugs used at the present time are costly and have low benefit-risk ratios.

Thus, there exists a need for antiinflammatory, analgesic and antipyretic herbal-based therapeutics which are cost-effective, safe, and efficacious, and with less or no side effects, so that it can be used for over prolonged period of time.

Natural products derived from plants and animals have offered a vast reservoir of materials, which have potential pharmacological effects on humans, and have been the sources for effective drugs. Most of the natural products are non-toxic and relatively inexpensive. Some of the herbal products have demonstrated therapeutic effects in treating various diseases or disorders. According to the World Health Organization (WHO), 4 billion people, i.e., about 80% of the world population, use herbal medicines for some aspects of health-related treatments. A recent study on trends in alternative medicine use show that there is a 47.3% increase in visits to alternative medicine practitioners from 1990 to 1997, with 629 million of total visits, exceeding 386 million total visits to all US primary care physicians in 1997. Herbal medicines represent the fastest growing segment among all of alternative medicines.

Herbal medicines can be used as botanical drugs and/or dietary supplements.

Botanical Drug

A botanical drug consists of vegetable materials, which may include plant materials, algae, macroscopic fungi, or combinations thereof. A botanical drug product may be available as (but not limited to) a solution (e.g., tea), powder, tablet, capsule, elixir, topical, or injection. In August 2000, US FDA has published draft guidance for industry botanical drug products.

Dietary Supplement

US Congress defined the term "dietary supplement" in the Dietary Supplement Health and Education Act (DSHEA) of 1994. A dietary supplement is a product taken by mouth that contains a "dietary ingredient" intended to supplement the diet. The "dietary ingredients" in these products may include: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on their label must not represent the product as a conventional food or a sole item of a meal or diet. Whatever their form may be, DSHEA places dietary supplements in a special category under the general umbrella of "foods," not drugs, and requires that every supplement be labeled a dietary supplement.

Technical speaking, an herb is a small, non-woody (i.e., fleshy stemmed), annual or perennial seed-bearing plant in which all the aerial parts die at the end of each growing season. As the word is more generally used and as it is used herein, an herb is any plant or plant part which has a medicinal use. Thus, the seeds, leaves, stems, flowers, roots, berries, bark, or any other plant parts that are used for healing are considered to be an herb.

Herbal medicines have been used for treating various diseases of humans and animals in many different countries for a very long period of time (see, e.g., Kessler et al., The Doctor's Complete Guide to Healing Medicines, Berkley Health/Reference Books (1996); Mindell, supra). Herbal medicines are available in many forms, (including capsules, tablets, or coated tablets; pellets; extracts or tinctures; powders; fresh or dried plants or plant parts; prepared teas; juices; creams and ointments; essential oils; or, as combinations of any of these forms) and administered by various methods (including orally, rectally, parenterally, enterally, transdermally, intravenously, via feeding tubes, and topically). They are prepared by different methods (including crude powders, decocted herbs to refined, concentrated and standardized extracts).

The health benefit from taking herbs varies due to the quality of the products and the knowledge of consumers on the products. Some of the botanical drug products are required to be used under a physician's supervision, particularly those indicated for serious diseases, although the majority of herbal medicines are generally regarded as safe. It is estimated that approximately 50 percent of the thousands of drugs commonly used and prescribed today are either derived from a plant source or contain chemical imitations of a plant compound (Mindell, E. R., Earl Mindell's Herb Bible, A Fireside Book (1992)).

A number of herbal compositions are known to be useful for treatment of various diseases and other health-related problems afflicting humans and animals. For example, U.S. Pat. No. 5,417,979 discloses a composition comprising a mixture of herbs, including species of *Stephania* and *Glycyrrhiza*, as well as their extracts, which is used as an appetite stimulant and for treatment of pain. Herbal compositions which include *Glycyrrhiza uralensis* have been found useful for treating eczema, psoriasis, pruritis and inflammatory reactions of the skin (U.S. Pat. No. 5,466,452). U.S. Pat. No. 5,595,743 discloses various herbs, such as licorice extract (*Glycyrrhiza*) and siegesbeckia, sophora, stemona and tetrandra herbs, which are useful for treatment of various mammalian diseases, including inflammation and rheumatoid arthritis. Ocular inflammation can be treated with the plant alkaloid tetrandrine (U.S. Pat. No. 5,627,195). In addition, U.S. Pat. No. 5,683,697 discloses a pharmaceutical composition having anti-inflammatory, anti-fever, expectorant or anti-tussive effect. The composition includes plants from *Melia, Angepica, Dendrobium, Impatiens, Citrus, Loranthus, Celosia, Cynanchum* and *Glehnia*. An herbal formulation comprising extracts of the roots, rhizomes, and/or vegetation of *Alphinia, Smilax, Tinospora, Tribulus, Withania* and *Zingiber* has been found having the effects of reducing or alleviating the symptoms associated with rheumatoid arthritis, osteoarthritis, reactive arthritis and reducing the production of proinflammatory cytokines (U.S. Pat. No. 5,683,698).

In the invention to be presented in the following sections, a herbal composition containing Radix Clematidis, Radix Angelicae Pubescentis, Rhizoma et Radix Notopterygii, Radix Saposhnikoviae, Radix Gentianae Macrophyllae are described. A herbal composition, further containing Radix Angelicae Sinensis, Rhizoma Chuanxiong, Cortex Eucommiae, and Radix Achyranthis Bidentatae, are described.

All the raw materials used for the complex herbal formulation are listed in the Chinese Pharmacopoeia. This herbal composition is particularly effective in treating and preventing inflammatory and rheumatic arthritic diseases in humans.

SUMMARY OF THE INVENTION

The present invention provides a first herbal composition which comprises Radix Clematidis, Radix Angelicae Pubescentis, Rhizoma et Radix Notopterygii, Radix Saposhnikoviae, and Radix Gentianae Macrophyllae. This herbal composition is effective to be used as a pharmaceutical composition for treatment of inflammatory and rheumatic arthritic diseases, such as acute or chronic rheumatoid arthritis, osteoarthritis, atrophic arthritis, chronic inflammatory arthritis, arthritis deformans, infectious arthritis, menopausal arthritis, arthritis mutilans, hypertrophic arthritis, suppurative arthritis, tubrculos arthritis or degenerative arthritis, in humans and livestock. It is also effective to be used as a dietary supplement for prevention and providing relief of symptoms of inflammatory and rheumatic arthritis. The preferred weight ratio of Radix Clematidis, Radix Angelicae Pubescentis, Rhizoma et Radix Notopterygii, Radix Saposhnikoviae, and Radix Gentianae Macrophyllae is about 1.2:1:1:1:1.

In this herbal composition, Radix Clematidis harvested from the root of the *Clematis chinensis* Osbeck, *Clematis hexapetala* Pall., *Clematis uhcinata* Champ., *Clematis armandi* Franch., *Clematis uncinata* Champ. Ex Benth., *Clematis meyeniana* Walp., *Clematis henryi* Oliv., *Clematis finetiana* Levl. Et Vant., *Clematis manshurica* or *Clematis paniculata* Thunb. Rupr. are preferred. In addition, the Radix Clematidis is also harvested from the root of *Smilax scobini-* caulis C. H. Wright, *Smilax* Stans Maxim., *Smilax sieboldi* Miq., *Veronicastrum sibiricum* (L.) Pennell, or *Inula nervosa* Wall.

In the herbal composition, wherein the Radix Angelicae Pubescentis is harvested from the root of *Angelica pubescens* Maxim. *F. bisserrata* Shan et Yuan, *Angelica pubescens* Maxim., *Angelica dahurica* (Fisch. Ex Hoffm.) Benth. et Hook. f. ex. Franch. Et Sav., *Angelica porphyrocaulis* Nakai et Kitag., *Heracleum hemsleyanum* Diels, *Heracleum lanatum* Michx. or *Aralia cordata* Thunb. In addition, Radix Angelicae Pubescentis in the herbal composition is also harvested from the root of *Angelica brevicaulis* L., *Angelica polyclada* Franch., *Heracleum yungningense* Hand.-Mazz., *Heracleum candicans* Wall. ex DC., *Aralia atropurpurea* Franch., or *Aralia henryi* Harms.

In the herbal composition, the Rhizoma et Radix Notopterygii is harvested from the rhizome and root of *Notopterygium incisum* Ting, *Notopterygium forbesii* Boiss, or *Notopterygium franchetii* Boiss are preferred.

In the herbal composition, the Radix Gentianae Macrophyllae is harvested from the root of *Gentiana macrophylla* Pall., *Gentiana crassicaulis* Duthie ex Burk., *Gentiana tibetica* King. are preferred. Additionally, the Radix Gentianae Macrophyllae in the herbal composition is also harvested from the root of *Gentiana straminea* Maxim., *Gentiana dahurica* Fisch., *Gentiana walujewii* Reg. et Schmalh, *Gentiana kaufinanniana* Reg. et Schmalh, *Gentiana Tianschanica* Ru. pr., or *Gentiana Siphonantha* Maxim. Ex Kusnez.

The present invention also provides a second herbal composition which comprises Radix Angelicae Sinensis, Rhizoma Chuanxiong, Cortex Eucommiae, and Radix Achyranthis Bidentatae. This composition also demonstrates preventive and therapeutic effects on inflammatory and rheumatic arthritic diseases, and can be used as either pharmaceutical composition for humans or livestock or as dietary supplement for humans. The preferred weight ratio of Radix Angelicae Sinensis, Rhizoma Chuanxiong, Cortex Eucommiae, and Radix Achyranthis Bidentatae is about 1.5:2:1:1.

It is preferable to combine the first and second herbal composition to achieve the maximal preventive and therapeutic effect of the herbs on alleviating the symptoms of or treating inflammatory and rheumatic arthritis.

To be used for pharmaceutical treatment, the herbal compositions are preferred to be orally given to patients at a daily dosage of 10 to 200 g per day in either a powder form or a liquid form, although alternatively the herbal compositions can be rectally, parenterally, enterally, transdermally, intravenously, via feeding tubes, and topically. To be used as dietary supplement, the herbal compositions are preferred to be orally given to a human at 0.1% to 15% by weight of the daily food consumption.

The present invention also provides processes for the herbal compositions. The herbal compositions can be produced in powder form or in liquid form. The powder form of the herbal composition is produced by mincing or pulverizing the herbs. The powder form can be further processed to form granules, tablets, or capsules. The liquid form of the herbal composition can also be added to tea, elixir, suspension, emulsion, syrup, aerosol, topical ointment, suppository, or sterile injection solution, to be used as beverage, topical ointment, rectal suppository, or as injection solution.

The liquid form of the herbal compositions is prepared by adding the powder of the herbs to a solvent, preferably distilled water, alcohol having 1 to 4 carbon atoms, and/or a mixture thereof. It is preferred that the solvent is about 0.5 to 20 times by volume, most favorably 5 to 10 times by volume, of the herbal powder. It is also preferred that the powder is enfleuraged in the solvent at a temperature of about 0° to 35° C., most favorably 15 to 25° C., for about 1 days to 3 months.

A preferred method to prepare a so-called "arthritis alcoholic liquor" is by adding about 700 kg of the herbal powder to about 3500 Liter of alcohol, preferably 50% ethanol, and stirring the mixture every 2 hours for about 3 days, and then adding 1500 L of distilled water to the mixture, followed by stirring every 2 hours for about 3 days.

BRIEF DESCRIPTION OF THE DRAWINGS

The invention may be better understood with reference to the accompanying drawings wherein.

DETAILED DESCRIPTION OF THE INVENTION

Figure 1:
FIG. 1. Photograph of the hands of a 53-year-old farmer (Example 5) with 20 years RA history taken on Feb. 24, 2003, showing swollen joint.

Traditional Chinese medicine has been in existence for more than two thousand years. It has a proven record of success for curing many kinds of diseases. Traditional Chinese medicine utilizes a variety of herbs and natural substances. Each herb/natural substance has its unique characteristics. By combining and balancing the unique characteristics of herbs, a doctor can prescribe a formulation with enhanced medicinal activities and with less or no toxicity by synergizing the medicinal effects among various herbs, while in the meantime, canceling out or neutralizing the toxic effects of the herbs.

The present invention provides two novel herbal compositions methods of using such compositions for preventing and/or relieving pain and inflammation due to inflammatory and rheumatic diseases. The two herbal compositions can be combined into one with enhanced preventive and/or therapeutic activities. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described below as follows:

Components of the Herbal Compositions

There are two herbal compositions in the present invention. The components of these two herbal compositions are described in Tables 1 and 2:

TABLE 1

Components of the First Herbal Composition

| Pharmaceutical Name | Botanical (Latin) Name | Chinese Name | Major Known Ingredients |
|---|---|---|---|
| Radix Clematidis | *Clematis Chinesis* Osbeck | Wei Ling Xian | Anemonin, anemonol, Kaempferol, Clematoside A, A', B, and C, sterols, Hederagenin, saponins, phenols, oleanolic acid |
| Radix Angelicae pubescentis | *Angelica pubescens* Maxim. | Du Huo | Angelol, angelicone, Glabralactone, bergapten, osthol, umbelliferone, scopolerin, angelic acid, tiglic acid, palmitic acid, sterols, stearic acid, Angelicin, Pimpinellin, Xanthotoxin, Sphondin, Isopimpinellin, Isobergapten, Psoralen, linolenic acid, oleic acid, glucose, essential oils |
| Rhizoma et Radix Notopterygii | *Notopterygium incisum* Ting ex H. T. Chang | Qiang Huo | Angelical |
| Radix Saposhnikoviae | *Saposhnikovia divaricata* (Turcz.) Schischk | Fang Feng | Mannitol, deltoin, 3'-O-angeloylhamaudol, 5-O-methylrisanrinol |
| Radix Gentianae macrophyllae | *Gentiana macrophylla* Pall. | Qin Jiao | Gentianine, Gentianidine, Gentialutine, Gentianaine, Gentioflavine. |

TABLE 2

Components of the Second Herbal Composition

| Pharmaceutical Name | Botanical (Latin) Name | Chinese Name | Major Known Ingredients |
|---|---|---|---|
| Radix Angelicae *Sinensis* | *Angelica sinensis* (Oliv.) Diels | Dang Gui | Butylidene phthalide, n-butylidene-phthalide, sequiterpenes, carvacrol, dihydrophthalic anhydride, n-Valerophenone-o-carboxylic acid, $\Delta^{2,4}$-Dihydrophthalic anhydride, sucrose, vitamin $B_{12}$, carotene, β-sitosterol |
| Rhizoma *Chuanxiong* | *Ligusticum chuanxiong* Hort. | Chuan Xiong | Tetramethylpyrazine, perlolyrine, ferulic acid, chrysophanol, sedanoic acid, 4-hydroxy-3-butyphthalide |
| Cortex Eucommiae | *Eucommia ulmoides* Oliv. | Du Zhong | Gutta-percha, aucubin, alkaloids, glycosides, potassium, vitamin C |
| Radix Achyranthis Bidentatae | *Achyranthes bidentata* Bl. | Niu Xi | Triterpenoid saponins, Ecdysterone, Inokosterone, Oleanolic acid |

The pharmaceutical names, as shown in the first column of Tables 1 and 2, are given the Latin binomial names. The part of the plant that is used for herb is identified in the first word of the binomial name. For example, Radix denotes that the "root" of the herb is used as the herbal component. Rizoma denotes that the "rhizome" of the herb is used as the herbal component. Cortex denotes that the "bark" of the herb is used as the herbal component.

Also, Tables 1 and 2 only listed the preferred species and preferred plant parts to be used for the herbal compositions, one skilled in the art readily recognizes that alternative plant species and alternative plant parts, as well as alternative geographic sources for the plants, will also satisfy the requirements of the composition. If herbs of an alternative species and/or plant part and/or plant origin were used to prepare the composition, then one skilled in the art could easily make any necessary adjustments in the preparation of the composition to account for the lower or higher concentrations of any particular active ingredient. For example, although Radix Clematidis (Wei Ling Xian) is preferred to be harvested from C*Clematis chinensis* Osbeck, Radix Clematidis from *Clematis hexapetala* Pall., *Clematis uhcinata* Champ., *Clematis armandi* Franch., *Clematis uncinata* Champ. Ex Benth., *Clematis meyeniana* Walp., *Clematis henryi* Oliv., *Clematis finetiana* Levl. Et Vant., *Clematis manshurica* or *Clematis paniculata* Thunb. Rupr has demonstrated similar therapeutic effects. Same applies to Radix Gentianae Macrophyllae (Qin Jiao), although Radix Gentianae Macrophyllae is preferred to be harvested from *Gentiana macrophylla* Pall., Radix Gentianae Macrophyllae harvested from *Gentianae straminea*

Maxim., *Gentiana crassicaulis* Duthie ex Burk, *Gentiana tibetica* King, or *Gentiana dahurica* Fisch. has similar therapeutic effective.

The herbal components used in the present invention are described as follows. These herbs are included in the official medicaments described in the Chinese Pharmacopoeia (2000), which is herein incorporated by reference in its entirety.

a. Radix *Clematidis* (Wei Ling Xian)

The dried root of *Clematis chinensis* Osbeck, *Clematis hexapetala* Pall., *Clematis uhcinata* Champ., *Clematis armandi* Franch., *Clematis uncinata* Champ. Ex Benth., *Clematis meyeniana* Walp., *Clematis henryi* Oliv., *Clematis finetiana* Levl. Et Vant., *Clematis manshurica* or *Clematis paniculata* Thunb. Rupr was used in the first herbal composition. The Radix Clematidis is also harvested from the root of *Smilax scobinicaulis* C. H. Wright, *Smilax* Stans Maxim., *Smilax sieboldi* Miq., *Veronicastrum sibiricum* (L.) Pennell, or *Inula nervosa* Wall. The roots were obtained from the Jiansu, Anhui, Zhejian, Shandong, Sichuan, Guangdong, and Fujian provinces of China.

b. Radix Angelicae Pubescentis (Du Huo)

The dried root of *Angelica pubescens* Maxim. *F. bisserrata* Shan et Yuan, *Angelica pubescens* Maxim., *Angelica dahurica* (Fisch. Ex Hoffin.) Benth. et Hook f ex. Franch. Et Sav., *Angelica porphyrocaulis* Nakai et Kitag., *Heracleum hemsleyanum* Diels, *Heracleum lanatum* Michx. or *Aralia cordata* Thunb was used in the first herbal composition. The Radix Angelicae Pubescentis is also harvested from the root of *Angelica brevicaulis* L., *Angelica polyclada* Franch., *Heracleum yungningense* Hand.-Mazz., *Heracleum candicans* Wall. ex DC., *Aralia atropurpurea* Franch., or *Aralia henryi* Harms. The roots were obtained from the Hubei, Sichuan and Jianxi provinces of China.

c. Rhizoma et Radix Notopterygii (Qiang Huo)

The dried stem tuber of *Notopterygium incisum* Ting, *Notopterygium forbesii* Boiss, or *Notopterygium franchetii* Boiss was used in the first herbal composition. The tubers were collected in the Qinghai, Sichuan, Yuannan, Gansu, Hubei and Shanxi provinces of China.

d. Radix Saposhnikoviae (Fang Feng)

The dried root of *Saposhnikovia divaricata* (Turcz.) Schischk is used in the composition. The roots were obtained from the east-north of China, and inner mongulia, HeBei, Shangdong, Henan, Shangxi, Shanxi, and Hunan provinces of China.

e. Radix Gentianae Macrophyllae (Qin Jiao)

The dried root of *Gentiana macrophylla* Pall., *Gentiana crassicaulis* Duthie ex Burk, *Gentiana tibetica* King was used in the first herbal composition. The Radix Gentianae Macrophyllae is also harvested from the root of *Gentiana straminea* Maxim., *Gentiana dahurica* Fisch., *Gentiana walujewii* Reg. et Schmalh, *Gentiana kaufmanniana* Reg. et Schmalh, *Gentiana Tianschanica* Ru. pr., or *Gentiana Siphonantha* Maxim. Ex Kusnez. The roots were obtained from the Helongjian, Liaolin, Inner Mongulia, Hebei, Shangxi, Shanxi, Henan, Ninxia, Gansu, Xinjiang, and Sichuan provinces of China.

f. Radix Angelicae Sinensis (Dang Gui)

The dried root of *Angelica sinensis* (Oliv.) Diels is used in the second herbal composition. The roots were obtained from the Gansu, Yuannan, Shanxi, Sichuan, Hubei and Guizhou provinces of China g. Rhizoma Chuanxiong (Chuan Xiong)

The dried stem tuber of *Ligusticum chuanxiong* Hort. was used in the second herbal composition. The tubers used in the example of the present invention were obtained from the Sichuan and Yuannan provinces of China h. Cortex Eucommiae (Du Zhong)

The dried bark of *Eucommia ulmoides* Oliv. was used in the second herbal composition. The barks were obtained from the Sichuan, Shanxi, Hubei, Henan, Guizhou, Yunnan, Jianxi, Gansu, Hunan and guanxi provinces of China.

i. Radix Achyranthis Bidentatae (Niu Xi)

The dried root of *Achyranthes bidentata* Bl. was used in the composition. The roots used in the example of the present invention were obtained from the Henan province of China.

In addition to the therapeutic effects of the herbs, the herbal composition described in the present invention also can be used as dietary supplement for alleviating symptoms associated with various rheumatoid and rheumatoid-like conditions and diseases, especially osteoarthritis and rheumatoid arthritis. The compositions of the present invention can also be used to control or relieve the symptoms of rheumatoid arthritis during its active stages and to prevent or slowdown articular deformity.

According to traditional Chinese medicinal theory, rheumatoid arthritis gives rise to pertinacious numbness. Thus, it takes a strong drugs, which not only can expel wind and remove dampness, but also can clear and activate the channels and collaterals, to contain the disease.

Among the components of the herbs used in the present invention, Radix Clematidis is the most important herb for its capability to expel wind and remove dampness, and to clear and activate the channels and collaterals. Rhizoma et Radix Notopterygii can expel upper wind dampness. Radix Angelicae Pubescenti can expel down wind dampness. Radix Saposhnikoviae can expel Taiyan channel wind dampness. Radix Gentianae Macrophyllae can not only expel wind and remove dampness, but also clear and activate the channels and collaterals. Thus, the combined effect of Radix Clematidis, Rhizoma et Radix Notopterygii, Radix Angelicae Pubescenti, Radix Saposhnikoviae, and Gentianae Macrophyllae in the first herbal composition provides the therapeutic function of expelling wind and removing dampness, the key factor for providing relief for inflammatory and rheumatic diseases.

Radix Angelicae Sinensis and Rhizoma Chuangxiong also have similar effects of expelling wind and removing dampness, and can strengthen the function of clearing and activating the channels and collaterals. They also can enrich the blood and promote blood circulation by removing blood stasis as ministers. Cortex Eucommiae and Radix Achyranthis Bidentatae have the effects of invigorating the liver and kidney so as to strengthen the bones and muscles and ensure proper downward flow of the drug as conductant. Thus, the combined use of Radix Angelicae Sinensis, Rhizoma Chuangxiong, Cortex Eucommiae, and Radix Achyranthis Bidentatae, also have therapeutic effects of providing relief of pain and inflammation associated with inflammatory and rheumatic diseases.

The combined use of the first and the second herbal compositions provide synergistic effects to enhance the function of treating inflammatory and rheumatic diseases.

The following examples are illustrative, but not limiting the scope of the present invention. Reasonable variations, such as those occur to reasonable artisan, can be made herein without departing from the scope of the present invention. Also in describing the invention, specific terminology is employed for the sake of clarity. However, the invention is not intended to be limited to the specific terminology so selected.

It is to be understood that each specific element includes all technical equivalents which operate in a similar manner to accomplish a similar purpose.

EXAMPLE 1

Components and Proportions of the Herbal Composition

The components and proportions of the herbs used in the combined first (as shown in Table 1) and second (as shown in Table 2) herbal compositions are shown in Table 3. It is understood that the proportions of herbs used in the herbal composition were provided as example only and are in no way to be construed as limiting the scope of the present invention from including any novel combination of the disclosed herbal and non-herbal components which have the intended effect of relieving the symptoms of pain, fever and inflammation, as discussed herein.

TABLE 3

Components and Proportions of the Herbal Compositions

| Ingredient | Weight (g) |
| --- | --- |
| Radix Clematidis | 12 g |
| Radix Angelicae Pubescentis | 10 g |
| Rhizoma et Radix Notopterygii | 10 g |
| Radix Saposhnikoviae | 10 g |
| Radix Gentianae Macrophyllae | 10 g |
| Radix Angelicae Sinensis | 20 g |
| Rhizoma Chuanxiong | 15 g |
| Cortex Eucommiae | 10 g |
| Radix Achyranthis Bidentatae | 10 g |

The herbal composition was prepared in two forms, a powder form or a liquid form, which are described as follows:

I. Method for Preparing a Powder Form of the Herbal Composition
 a. Individually weigh the herbs;
 b. Wash and dry the herbs;
 c. Cut the dried herbs into small pieces.
 d. Grind the dry herbs into powder;
 f. Pass the powder through an about 100 mesh;
 g. Pour about 0.3 g of the powder into a capsule.

II. Method for Preparing an Alcoholic Liquor
 Alcoholic Liquor:
 a. Put 700 kg powder prepared in (I) into a 5000 L container;
 b. Add 3500 L 50 degree liquor into the container and stir every 2 hours for 3 days;
 c. Add 1500 L water into the container and stir every 2 hours for 3 days;
 d. Filtrate residue and collect the supernatant For the preparation of the liquid extract, the powder form of the herbal composition were mixed with 0.5 to 20-fold of a solvent. The preferred solvent was 5 to 10-fold volume of distilled water, or alcohols having 1 to 4 carbon atoms (such as methanol, ethanol and the like), or a mixture thereof. Preferably, the mixture of ethanol and water, more preferably with the ratio of 1:1 to 1:9 was used as the solvent. The herbal powder and the solvent were enfleuraged at the temperature ranging from 0 to 35° C., preferably from 15° C. to 25° C. (room temperature), for the period ranging from 12 hours to 5 months, preferably 1 day to 3 months to obtain the liquid extract of the herbal composition. The liquid extract was further filtered to remove the remaining herbal powder from the solution. The liquid form of the herbal composition is the filtrate of the liquid extract.

EXAMPLE 2

Botanical Drug and Pharmaceutical Formulations

The herbal compositions of this invention can be used in the form of a botanical drug or as a medicinal preparation, for example, in solid, semi-solid or liquid form which contains the herbal composition of the present invention, as an active ingredient, in admixture with an organic or inorganic carrier or excipient suitable for external, enteral or parenteral applications.

The herbal composition can be added with conventional pharmaceutically-acceptable carriers, adjuvants. Examples of the pharmaceutically-acceptable carriers, adjuvants or diluents, include, not are not limited to, lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil.

A pharmaceutical formulation containing the herbal composition can also be prepared by adding fillers, anti-agglutinating agents, lubricating agents, wetting agents, flavoring agents, emulsifiers, preservatives and the like to the herbal composition. The herbal composition of the invention may be formulated so as to provide quick, sustained or delayed release of the active ingredient after their administration to a patient by employing any of the procedures well known in the art. For example, the herbal compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing the present herbal composition can be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The herbal composition of the present invention in pharmaceutical dosage forms can be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 0.001-10 g/kg, preferably, 0.01 to 1 g/kg by weight/day or 0.1 to 200 g per day of the herbal composition. The dose may be administered in a single or multiple doses per day. In terms of pharmaceutical composition, the herbal composition should constitute between 0.01 to 99% by weight, preferably 50 to 90% by weight based on the total weight of the pharmaceutical composition.

The pharmaceutical composition of present invention can be administered to a subject animal such as mammals (livestock [cow, pig, horse etc.], domestic animals [such as dogs, cats], or human) via various routes. All modes of administration are contemplated, for example, administration can be made orally, rectally or by intravenous, intramuscular, subcutaneous, intracutaneous, intrathecal, epidural or intracerebroventricular injection.

The active ingredient may be compounded, for example, with the usual non-toxic pharmaceutically acceptable carriers for tablets, pellets, capsules, suppositories, solutions, emulsions, suspensions, and any other form suitable for use. Formulations of the present invention encompass those which include the exemplified carrier talc, as well as carriers other than talc such as water, glucose, lactose, gum acacia, gelatin, mannitol, starch paste, magnesium trisilicate, corn starch, keratin, colloidal silica, potato starch, urea and other carriers suitable for use in manufacturing preparations, in solid, semisolid or liquid form and in addition auxiliary, stabilizing, thickening and coloring agents and perfumes may be used.

For preparing solid compositions such as tablets or capsules, the principal active ingredients are mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid pre-formulation composition containing a substantially homogeneous mixture of a composition of the present invention, or a non-toxic pharmaceutically acceptable salt thereof. When referring to the pre-formulation compositions as substantially homogenous, it is meant that the active ingredients are dispersed evenly throughout the composition so that the composition may be readily subdivided into equally effective unit dosage forms such as tablets, pills and capsules. This solid pre-formulation composition is then subdivided into unit dosage forms of the type described above containing about 0.4 mg of the herbal composition of the present invention, preferably in capsules. The tablets or pills of the novel composition can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate.

The liquid forms, in which the novel composition of the present invention may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the composition may take the form of tablets or lozenges formulated in conventional manners.

The active compounds may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

The herbal composition of the present invention is suitable for use as a health food/dietary supplement, by optionally adding a sitologically acceptable additive to the composition. The herbal composition of the present invention has the capability of preventing and alleviating pain and inflammation associated with inflammatory and rheumatic arthritic diseases, e.g., rheumatic arthritis.

The health food/dietary supplement composition for preventing arthritic diseases could contain about 0.01 to 95 w/w %, preferably 0.5 to 80 w/w % of the herbal composition of present invention based on the total weight of the composition.

The herbal composition can also be added to food, additive or beverage for prevention of arthritic diseases. For the purpose of preventing arthritic diseases, wherein, the amount of above described extract or compound in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of present invention contains above described extract or compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/W % per 100 w/w % present composition.

Examples of addable food comprising aforementioned extract therein are various food, beverage, gum, vitamin complex, health improving food and the like.

The herbal composition of the present invention is also suitable to be used in a feed for livestock to prevent inflammatory and rheumatic arthritic diseases, e.g., rheumatic arthritis. A sitologically acceptable additive is preferred to be added to the herbal composition.

Inventive feed additive can be added with the range from 0.01 to 95 w/w %, preferably 0.5 to 80 w/w % of the above herbal extract in feed to treat and prevent arthritic diseases of the livestock.

EXAMPLE 3

Clinical Study Anti-Rheumatoid Arthritis Liquor (ARL)

I. Clinical Data a. Subjects

Outpatients with active rheumatoid arthritis, according to the classification criteria of the American Arthritis College, without other significant medical conditions were recruited. 40 patients were recruited, 7 male and 33 female. Their ages were ranged from 28-67 years old with average of 46.8 years old. The disease duration of the patients ranged from 0.4 to 13 years. All the patients had previously taken a variety of other anti-rheumatic herbal medicine, but there was no improvement or just in relapse.

b. Treatment

Forty patients assigned randomly for treatment with ARL or active control. Safety and compliance were monitored every 2 weeks with complete outcome evaluation at 4, 8, and 12 weeks. Observe group, 20 patients, was treated with ARL (30 ml/d). It was taken before sleep or equally divided to be taken in the morning and evening. In the mean time, active control group, 20 patients, was treated with the combination of Methotrexate (MTX) (once a week, 7.5 mg), Mian IV (a recipe contain 28 ingredients, a house made medicine for RA in this hospital, one preparation per day) and one NSAID, such as Fenbid, Arthrotec, etc. The combination was one of the best treatments for RA we could provide in our clinic in terms of both safety and efficacy.

c. Outcome Measurements

The outcome measurements for the both groups were divided to signs and symptoms, including: rest pain assessment, duration of morning stiffness, number of tender joint and the index of tenderness, number of swelling joints and the swelling index, grip strength, joint function, erythrocyte sedimentation rate, C reaction protein, and rheumatoid factor. The individual parameter improvement was calculated through the following formula:

$$\frac{\text{Pre-treatment value} - \text{post treatment value}}{\text{Pre-treatment value}} \times 100\%$$

The total improvement was used to compare the efficacy between the two groups. In order to accurately reflect the drug efficacy, 50% improvement, 75% improvement, and 100% improvement (R50, R75 and R100) were used as statistical endpoint for efficacy.

The side effects were observed and recorded including stomach pain, stomach burning, headache, rash, drug tolerance, and hepatic and renal function, and blood routine tests, etc.

d. Statistics t-test was used to analyze the significance of the differences between the observe group and active control group.

e. Results

All patients were completed the scheme. There was no dropout occurred.

i. Comparison of the Treatment Effects Between Anti-Rheumatoid Arthritis Liquor (ARL) and Methotrexate (MTX), (see Table 4).

TABLE 4

Comparison of the Treatment Effects of ARL and MTX

| Time(weeks) | Effect (improvement) | ARL(number(%)) | MTX(number(%)) |
|---|---|---|---|
| 4 | 50% | 5 (25)* | 0 |
|   | 75% | 10 (50)* | 0 |
|   | 100% | 5 (25)* | 0 |
| 8 | 50% | 2 (10)* | 0 |
|   | 75% | 6 (30)* | 0 |
|   | 100% | 12 (60)* | 0 |
| 12 | 50% | 1 (5)* | 9 (45) |
|   | 75% | 6 (30)* | 0 |
|   | 100% | 13 (65)* | 0 |
| 26 | 50% |  | 8 (40) |
|   | 75% |  | 10 (50) |
|   | 100% |  | 0 |
| 52 | 50% |  | 0 |
|   | 75% |  | 15 (75) |
|   | 100% |  | 5 (25) |

*$P < 0.01$ i.i. Comparison of the Time Required for Symptom Improvement between ARL Treatment Group and MTX Treatment Group, (See Table 5).

During the drug administration periods of the both groups, there was significant gastrointestinal reaction, allergy, changes in hepatic and renal function and blood cytologic abnormality.

f. Discussion

TABLE 5

Comparison of the Time Required for Improvement Between ARL and MTX

| Group | R50(week) | R75(week) | R100(week) |
|---|---|---|---|
| ARL | 2.4 ± 1.14* | 3.2 ± 0.90* | 6.8 ± 2.61* |
| MTX | 15.2 ± 5.43 | 27.7 ± 10.5 | 47.2 ± 10.7 |

*$P < 0.001$ g. Side Effects

During the observation periods of the both groups, there was no apparent gastrointestinal reaction, allergy, and changes in liver, kidney function and blood cytologic changes observed.

h. Discussion

Rheumatoid arthritis is a chronic inflammatory disease that primarily affects the joints and surrounding tissues but also affects other organ systems within the body. It is a systemic disorder.

Pharmacotherapy for rheumatoid arthritis (RA) consists of non-steroidal anti-inflammatory drugs (NSAIDs), disease-modifying anti-rheumatic drugs (DMARDs) and corticosteroids.

NSAIDs are generally prescribed as pain killer. Considerable progress has made as the recent introduction of the cyclo-oxygenase 2 (Cox-2) inhibitors which significantly reduce side effects usually accompanied with traditional NSAIDs. However, there is more and more cardiovascular concerns over COX-2 inhibitors.

There are several new DMARDs available on the market. There are Arava (leflunomide); tumor necrosis factor (TNF) alfa inhibitors, Remicade and Enbrel (etanercept); and interleukin-1 receptor a antagonist, Kineret. However, the efficacy and safety of those new launches are still raising concerns. Regarding the cost the efficacy, Methotrexate (MTX) is still the most useful DMARD for RA at the present time around the world.

MTX usually requires 12-24 weeks to show some clinical effect and long term usually requires 1-3 years of administration. Because of long term administration, there have been reports concerning the toxic and side effects of MTX toward blood, liver and kidney, etc.

In this clinical trial, it was shown that ARL required shorter time to show clinical effectiveness. Four weeks after administration, it was able to make 50% RA patient to have 75% improvement on signs and symptoms (R75) and 25% RA patients to reach R100. Eight weeks after administration, 25% RA patients reached R75 and 60% RA patients reached R100. For the combination of oral MTX and NSAID, 12 weeks after administration, 45% RA patients reached R50; 26 weeks after administration, 40% RA patients reached R50 and 50% RA patients reached R75; 52 weeks after administration, 75% RA patients reached R75 and 25% RA patients reached R100. The efficacy differences between the two groups was extremely significant, P<0.01.

For the time required to improve the signs and symptoms of RA patients, ARL required 1-4 weeks to reach R50, 3.2 weeks for R75, and 4-12 weeks for R100. In contrast, the combination of MTX and NSAID required 8-12 weeks to reach R50, 20-32 weeks for R75 and 52 weeks for R100.

Through our clinical observation, there were no severe toxic and side effects observed in the ARL group. The patients who were not used to drink alcohol can equally divide the amount of drug into two, and take them separately in the morning and evening.

i. Conclusion

Based on this clinical trial, ARL is a fast acting drug for RA, it is able to let 65% of patients reach R100. It is clear superior than the methotrexate and NSAID combination. However, her long term efficacy need to be further investigated.

EXAMPLE 4

Clinical Study of Anti Rheumatoid Arthritis Capsule

Anti-Rheumatoid Arthritis Capsule (ARC) is a capsule made of the powder form of the herbal composition of the present invention in accordance with the components and method shown in Example 1. To assess the basic efficacy and side effect of ARC, an open, randomized and active controlled clinical trial was carried out.

Outpatients with active rheumatoid arthritis, according to the classification criteria of the American Arthritis College, without other significant medical conditions were recruited. Patients assigned randomized to treatment with ARC or active control. Safety and compliance were monitored every 2 weeks with complete outcome evaluation at 4, 8, and 12 weeks.

Thirty-six (36) typical active RA patients were selected and randomly divided into two groups. Observe group, 18 patients, was treated with ARC (4 capsules t.i.d., each capsule is about 0.3 g). In the mean time, 18 patients in the active control group were treated with the combination of Methotrexate (once a week, 10 mg), Folic acid (daily, 5 mg) and Arthrotec (b.i.d. 50 mg). The combination was one of the best treatments for RA in our clinic in terms of both safety and efficacy.

All the patients were treated and observed for 12 weeks. The improvement was denoted as either R50, R75 or R100 reflecting either an improvement to the 50%, 75%, or 100% level in the parameters based on the improvements of signs and symptoms including rest pain assessment, duration of morning stiffness, number of tender joint and the index of tenderness, number of swelling joints and the swelling index, grip strength, joint function, erythrocyte sedimentation rate, C reaction protein, and rheumatoid factor. From the outcome of the 36 patients treated with both ARC and active control, following results were recorded:

1. Four weeks after treatment, there was 44.5% patients achieved 50% response (R50) in the observe group; in the contrast, only 11.1% patients achieved R50 in the active control group. (p<0.01).

2. Eight weeks after treatment, there was 33.3% patients achieved 75% response (R75) and 27.8% patients achieved R50 in the observe group; still only 11.1% patients achieved R50 in the active control group.

3. Twelve weeks after treatment, there was 33.3% patients achieved 100% response (R100), which is similar to the statue of complete clinical response and 61.1% patients achieved R75 in the observe group; there was 11.1% patients achieved R75 and 55.5% patients achieved R50 in the active control group. (p<0.01).

4. During the observation, psychoneurological symptoms self-sensed by patients; gastrointestinal symptoms; blood pressure; routine blood and urine tests; liver and renal function test were performed. There was no abnormal reaction reported from both the patients and the lab test in the ARC group; however in the active control group, there are 3 patients complained about stomachalgia.

The Result of the Trial (See Table 6)

TABLE 6

Clinical Trial Results of ARC

| Time(weeks) | improvement (%) | Observed Group (ARC) (number(%)) | MTX Group (number(%)) |
|---|---|---|---|
| 4 | 50% | 8 (44.5) | 2 (11.1) |
|   | 75% | 0 | 0 |
|   | 100% | 0 | 0 |
| 8 | 50% | 5 (27.8) | 2 (11.1) |
|   | 75% | 6 (33.3) | 0 |
|   | 100% | 0 | 0 |
| 12 | 50% | 0 | 10 (55.5) |
|   | 75% | 11 (61.1) | 2 (11.1) |

Based on the results shown above, ARC, like ARL, was effective for RA and lack of the severe side effects shown by other RA drugs. From the data shown above, it appeared that ARC alone could be a potential promising new treatment for rheumatoid arthritis with good efficacy and safety.

EXAMPLE 5

Case Study

The patient was a 53 years old male farmer with about 20 years RA history. At the time when the study began, only diclofenac rectal suppository was used by him. He had used many different drugs before but could not recall the names of the drugs.

On 24 Feb., 2003, he was blood tested and hand picture taken. (See FIG. 1)

ESR: 24 mm/h, RF Ig G Ig M and Ig A: all negative. ASO: negative (50, normal<200 IU/ml).

The patient complained long duration of morning stiffness, rest pain, fatigue and apparent swelling on his hand. He was most of time staying in bed.

The patient started to take our herbal drug (ARL) 70 mu day besides the continuation of diclofenac rectal suppository.

Figure 2:
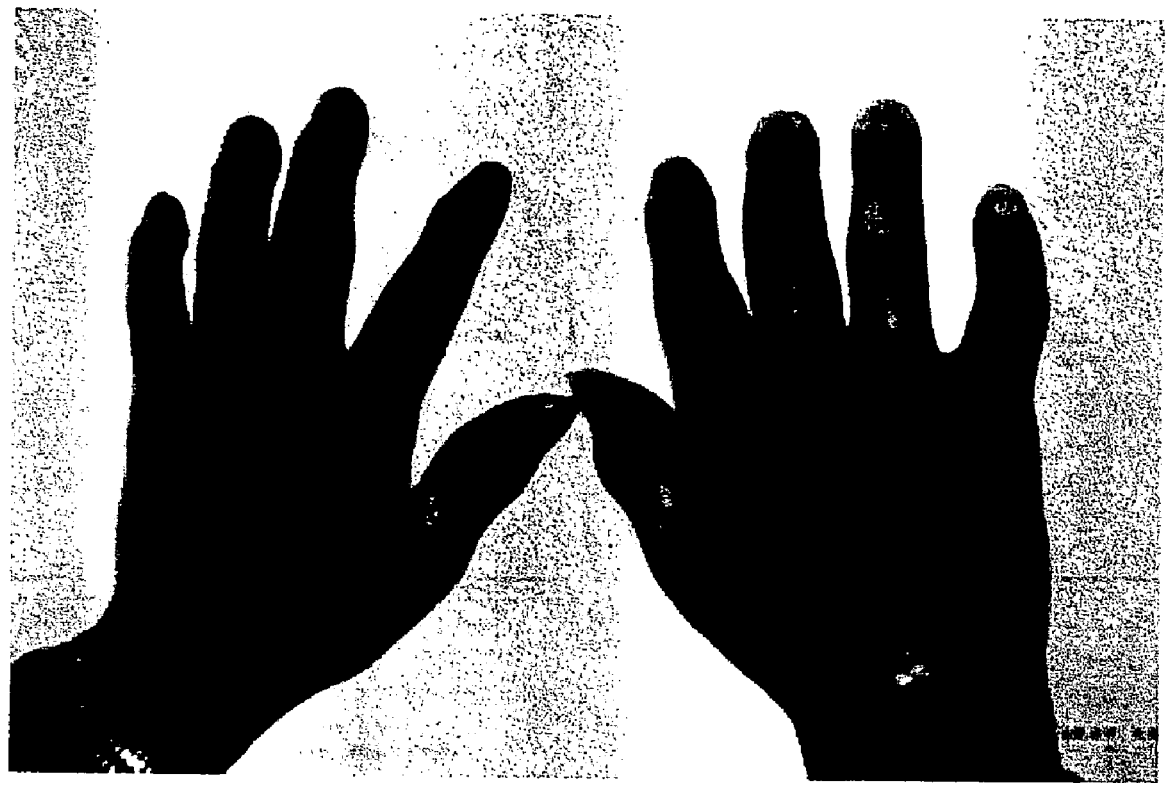
FIG. 2. Photograph of the hands of the farmer (Example 5) taken on Mar. 3, 2003, after he took the herbal composition (extract) of the present invention (70 ml/day) for about 1 week. The swelling of his hands was remarkably shrunken.

On 3 Mar., 2003, as the swelling of his hands was remarkably shrunken, photo of his hands were taken. (See FIG. 2).

Figure 3:
FIG. 3. Photograph of the hands of the farmer (Example 5) taken on May 19, 2003, after he continuously took the herbal composition (extract) of the present invention (70 ml/day) for about 3 months. There was no pain and no swollen joint in his hands.

On 19 May, 2003, the patient revisited. His blood was tested and hand picture was photographed. (See FIG. 3).

We were told that his morning stiffness disappeared. There was no pain and swollen joint in his hands. However, his knee was swelling and still in pain, so diclofenac rectal suppository was continued. When he stopped using diclofenac, only knee joints were in pain. He could start raising pigs again.

Blood test: RF: negative (10.9, normal <15 IU/ml), ESR: 48(normal<15 mm/h), Blood Uric acid: 649.5 umol/L (normal: 150-420 mmol/L)

A week later, the herbal drug was discontinued.

Figure 4:
FIG. 4. Photograph of the hands of the farmer (Example 5) taken on Aug. 8, 2003, after he discontinued to took the herbal composition (extract) of the present invention for about 3 months. There was no pain and no swollen joint in his hands.

On Aug. 8, 2003, his hands photo was taken again. (See FIG. 4). We were told that his morning stiffness disappeared. There was no pain and swollen joint in his hands. However, his knee was still swelling and in pain, so that the use of diclofenac rectal suppository was continued. When he stopped using diclofenac, only knee joints were in pain.

It should be understood that the foregoing discussion and examples merely present a detailed description of certain preferred embodiments. It therefore should be apparent to those of ordinary skill in the art that various modifications and equivalents can be made. Patent applications and references that are identified above are incorporated by reference in their entirety.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and in general, the principles of the invention and including such departures from the present disclosure as come within known or customary practice within the art to which the invention pertains and as may be applied to the essential features hereinbefore set forth and as follows in the scope of the appended claims.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An herbal composition for treating inflammatory and rheumatoid diseases in a mammal, comprising:
   an active ingredient consisting essentially of Radix Clematidis, Radix Angelicae Pubescentis, Rhizoma et Radix Notopterygii, Radix Saposhnikoviae, and Radix Gentianae Macrophyllae at a weight ratio of about 1.2:1:1:1:1.

2. The herbal composition according to claim 1, wherein said mammal is a human.

3. The herbal composition according to claim 1, wherein said herbal composition is formulated for oral administration at a dosage of about 0.1 to 200 g per day.

4. The herbal composition according to claim 1, wherein said mammal is a domestic animal.

5. The herbal composition according to claim 1, wherein said herbal composition is formulated as a dietary supplement.

6. The herbal composition according to claim 1, wherein said inflammatory and rheumatoid diseases are acute or chronic rheumatoid arthritis, osteoarthritis, atrophic arthritis, chronic inflammatory arthritis, arthritis deformans, infectious arthritis, menopausal arthritis, arthritis mutilans, hypertrophic arthritis, suppurative arthritis, tuberculous arthritis or degenerative arthritis.

7. The herbal composition according to claim 1, wherein said herbal composition reduces pain in said mammal.

8. The herbal composition according to claim 1, wherein said herbal composition improves joint health and flexibility in said mammal.

9. The herbal composition according to claim 1, wherein said herbal composition is in a liquid extract form or a powder form.

10. The herbal composition according to claim 9, wherein said liquid extract form of said herbal composition is prepared by extracting said mixture of herbs in a solvent, wherein said solvent is distilled water, alcohol having 1 to 4 carbon atoms, or a mixture thereof.

11. The herbal composition according to claim 9, wherein said powder form of said herbal composition is prepared by pulverizing said mixture of herbs.

12. The herbal composition according to claim 11, wherein said powder form of said herbal composition is further processed into granule, tablet or capsule.

13. The herbal composition according to claim 10, wherein said liquid form of said herbal composition is added to tea, elixir, suspension, emulsion, syrup, aerosol, topical ointment, suppository, or sterile injection solution.

14. The herbal composition according to claim 10, wherein said herbal composition is formulated for oral, rectal, parenteral, enteral, transdermal, intravenous, topical or feeding tube administration.

15. The herbal composition according to claim 1, wherein said Radix Clematidis is harvested from the root of *Clematis chinensis* Osbeck, *Clematis hexapetala* Pall., *Clematis uhcinata* Champ., *Clematis armandi* Franch., *Clematis uncinata* Champ. Ex Benth., *Clematis meyeniana* Walp., *Clematis henryi* Oliv., *Clematis finetiana* Levl. Et Vant., *Clematis manshurica, Clematis paniculata* Thunb. Rupr., *Smilax scobinicaulis* C. H. Wright, Smilax Starts Maxim., Smilax sieboldi Miq., *Veronicastrum sibiricum*(L.) Pennell, or *Inula nervosa* Wall.

16. The herbal composition according to claim 1, wherein said Radix Angelicae Pubescentis is harvested from the root of *Angelica pubescens* Maxim. F. bisserrata Shan et Yuan, *Angelica pubescens* Maxim., *Angelica dahurica* (Fisch. Ex Hoffm.) Benth. et Hook. f. ex. Franch. Et Say., *Angelica porphyrocaulis* Nakai et Kitag., *Heracleum hemsleyanum* Diels, *Heracleum lanatum* Michx., *Aralia cordata* Thunb., *Angelica brevicaulis* L., *Angelica polyclada* Franch., *Heracleum yungningense* Hand.-Mazz., *Heracleum candicans* Wall. ex DC., *Aralia atropurpurea* Franch., or *Aralia henryi* Harms.

17. The herbal composition according to claim 1, wherein said Rhizoma et Radix Notopterygii is harvested from the rhizome and root of *Notopterygium incisum* Ting, *Notopterygium forbesii* Boiss, or *Notopterygium franchetii* Boiss.

18. The herbal composition according to claim 1, wherein said Radix Gentianae Macrophyllae is harvested from the root of *Gentiana macrophylla* Pall., *Gentiana crassicaulis* Duthie ex Burk., *Gentiana tibetica* King., *Gentiana straminea* Maxim., *Gentiana dahurica* Fisch., *Gentiana walujewii* Reg. et Schmalh, *Gentiana kaufmanniana* Reg. et Schmalh, *Gentiana Tianschanica* Ru. pr., or *Gentiana Siphonantha* Maxim. Ex Kusnez.

19. An herbal composition for treating inflammatory and rheumatoid diseases in a mammal, comprising:
    an active inaredient consisting essentially of Radix Clematidis, Radix Angelicae Pubescentis, Rhizoma et Radix Notopterygii, Radix Saposhnikoviae, Radix Gentianae Macrophyllae, Rhizoma Chuangxiong, Radix Angelicae Sinensis, Cortex Eucommiae, and Radix Achyranthis Bidentatacasin in a weight ratio of about 1.2:1: 1:1:1:1.5:2:1:1.

20. A process for preparing a powder form of an herbal composition comprising:
    pulverizing the active ingredient of claim 1 into a powder form of said herbal composition.

21. A process for preparing a liquid form of an herbal composition comprising:
    pulverizing the active ingredigent of claim 1 into a powder form of said herbal composition;
    adding said powder form of said herbal composition to a solvent to produce a liquid extract of said herbal composition; wherein said solvent is distilled water, alcohol having 1 to 4 carbon atoms, or a mixture thereof;
    collecting said liquid form of said herbal composition by filtering said powder form of said herbal composition out of said liquid extract.

22. The process according to claim 21, wherein said solvent is about 0.1 to 20 times by volume of said powder.

23. The process according to claim 21, wherein said powder is enfleuraged in said solvent at a temperature of about 0° to 35° C. for about 1 days to 3 months.

24. The process according to claim 21, comprising:
    adding said powder form of said herbal composition to an alcohol to form a solvent mixture; wherein said alcohol is ethanol;
    stirring said solvent mixture about every 2 hours for about 3 days to form an herbal-solvent mixture; adding distilled water to said herbal extract mixture and stirring every 2 hours for about 3 days to form an herbal extract mixture; and
    filtering said powder form of said herbal composition out of said herbal extract mixture to obtain said liquid form of said herbal composition.

25. The process according to claim 22, wherein said alcohol is about 1-10 times by volume of said powder of said herbal composition by weight.

26. The process according to claim 22, wherein said alcohol is about 2-3 times by volume of said distilled water by volume.

* * * * *